US009788990B2

(12) United States Patent
Arkada (10) Patent No.: US 9,788,990 B2
(45) Date of Patent: Oct. 17, 2017

(54) DEVICE FOR CORRECTING INGROWING FOOT NAILS AND A METHOD FOR COSMETIC CORRECTION OF INGROWING FOOT NAILS

(71) Applicant: ARKADA LICENCE SP. ZO.O., Nowa Sol (PL)

(72) Inventor: Adrian Arkada, Nowa Sol (PL)

(73) Assignee: ARKADA LICENSE SP .ZO.O., Zielona Gora (PL)

( * ) Notice: Subject to any disclaimer, the term of this patent is extended or adjusted under 35 U.S.C. 154(b) by 507 days.

(21) Appl. No.: 14/350,368

(22) PCT Filed: Oct. 13, 2012

(86) PCT No.: PCT/EP2012/070354
§ 371 (c)(1),
(2) Date: Apr. 8, 2014

(87) PCT Pub. No.: WO2013/053933
PCT Pub. Date: Apr. 18, 2013

(65) Prior Publication Data
US 2014/0350448 A1    Nov. 27, 2014

(30) Foreign Application Priority Data

Oct. 14, 2011  (PL) .......................................... 396644
Dec. 23, 2011  (PL) .......................................... 397548
Mar. 15, 2012  (PL) .......................................... 398459

(51) Int. Cl.
*A61F 5/11*        (2006.01)
*A45D 29/00*    (2006.01)
(Continued)

(52) U.S. Cl.
CPC ................ *A61F 5/11* (2013.01); *A45D 29/00* (2013.01); *A61F 5/019* (2013.01); *A61F 2013/00353* (2013.01)

(58) Field of Classification Search
CPC .. A61F 5/11; A61F 5/019; A61F 2013/00353; A45D 29/00; A45D 29/02; A45D 29/023; A45D 29/026; A45D 29/22
(Continued)

(56) References Cited

U.S. PATENT DOCUMENTS 1,420,085 A  *  6/1922  Figielek .................... A61F 5/11
                                                                        602/31
1,772,130 A      8/1930  Crenshaw
(Continued)

FOREIGN PATENT DOCUMENTS

CN          201189225 Y        2/2009
DE              4207797 A1      9/1992
JP          2010172687 A        8/2010

*Primary Examiner* — Keri J Nelson
(74) *Attorney, Agent, or Firm* — Mark M. Friedman (57) ABSTRACT

A device for correcting ingrowing foot nails. It comprises a base (101; 201; 301), on which there are mounted means (111, 112; 211, 212; 311) for immobilizing the toe with respect to the base (101; 201; 301), means (121; 221; 321) pressing the middle portion of the nail towards the base (101; 201; 301), slidable and pivotable means (131, 132; 231, 232; 331) for manipulating at the lateral edge of the nail and slidable and pivotable means (141; 241, 242; 341) for manipulating at the front portion of the nail.

16 Claims, 6 Drawing Sheets

(51) Int. Cl.
*A61F 5/01* (2006.01)
*A61F 13/00* (2006.01)

(58) Field of Classification Search
USPC ........ 602/23, 30, 31, 22; 128/845, 846, 869, 128/878–880, 882
See application file for complete search history.

(56) References Cited

U.S. PATENT DOCUMENTS

| | | |
|---|---|---|
| 1,917,794 A | 7/1933 | Brown |
| 6,824,511 B1 * | 11/2004 | Bell ..................... A61B 17/02 600/227 |
| 8,337,443 B2 * | 12/2012 | Harada .................. A61F 5/11 602/23 |
| 8,517,966 B2 * | 8/2013 | Erdogan ................ A61F 5/11 602/23 |
| 2010/0137771 A1 | 6/2010 | Harada |

* cited by examiner

DEVICE FOR CORRECTING INGROWING FOOT NAILS AND A METHOD FOR COSMETIC CORRECTION OF INGROWING FOOT NAILS

TECHNICAL FIELD

The present invention relates to tools for correcting ingrowing foot nails and methods for cosmetic correction of ingrowing foot nails.

BACKGROUND ART

There are known various devices and methods for correcting ingrowing foot nails, most typically toe nails.

A Chinese utility model CN20082012494U presents an ingrown nail double-hook correction device, formed by a steel wire with certain length, wherein the two ends of the steel wire are respectively provided with an ingrown nail hook; two ingrown nail hooks are positioned at the front end of the correction device and are arranged side by side; and the back end of the correction device is a closed-type straight line or a closed-type arc-shaped line.

In turn, the device for correcting ingrowing toenails known from a German patent application DE4207797 consists of two short lengths of wire. Each length of wire has a hook formed at each end. The wires are placed on the surface of the nail with one of the hooked ends of each wire fitting under the edge of one side of the toe nail. The two wires are then fastened to each other by a third wire or by a thread made of plastics. This third wire or thread passes around the hooks at the free ends of the two wires and at the same time holds them to the toe nail.

The instrument for correcting ingrowing toenails known from the German patent application has a component placed on the toenail surface. A nickel-titanium alloy can be used as the material. Alternatively it can consist of wire or strip. It can comprise a holding portion secured to the nail and securing a correcting one which acts on the nail in the correcting direction.

Another correcting device for ingrowing toenails is known from a Japanese patent application JP2010172687. It includes a flat-forming part sliding to a nail fold part deformed by ingrowing nail into a curved shape to correct the ingrown nail to an almost flattened nail shape and a correction-acting part which obtains correction action by securing the ingrown nail after further sliding a correction-acting member and inserting the ingrown nail almost flattened by the flat-forming part into a gap.

A French patent application FR2639219 describes a device for correcting nail deformities, which comprises a T-shaped part which is adjustably attached to support and has curved arms in which corrective element is removably mounted. Each part of the corrective element is bent inwards to form a groove so that the two parts may be fixed over the side edges of the nail.

A US patent application U.S. Pat. No. 1,917,794 presents a finger tip and nail shaper, which has tip shaper of channel formation open at its inner end with the outer end closed by an arched and curved wall, curved spring arms carried by the channel member for attaching the same to a finger tip and a nail shaper supported by said curved spring arms.

The devices described above are configured for mounting on the nail and for carrying on the toe for a long time, lasting typically for several weeks, which is highly problematic and uncomfortable for the user.

It would be advantageous to provide a device and method for cosmetic correction of ingrown nails, which would allow quicker and easier correction of nail.

DISCLOSURE OF THE INVENTION

The object of the invention is a device for correcting ingrowing foot nails, the device comprising a base, on which there are mounted means for immobilizing the toe with respect to the base, means pressing the middle portion of the nail towards the base, slidable and pivotable means for manipulating at the lateral edge of the nail and slidable and pivotable means for manipulating at the front portion of the nail.

Preferably, it comprises two opposite supports mounted on the base, wherein on the first support there are mounted two screws for pressing the toe and two slidable and pivotable tools for manipulating at the lateral edge of the nail, which are positioned symmetrically with respect to a lever for pressing the nail, and wherein the second support comprises pivotable and slidable tools for manipulating at the front portion of the nail.

Preferably, the lever for pressing the nail is mounted pivotably in the first support, and the pressing force is adjustable by a screw for regulating the pressing of the nail.

Preferably, the means for manipulating at the lateral edge of the nail are held in spheroidal joints tightenable by blocking screws.

Preferably, the means for manipulating at the front part of the nail are held in spheroidal joints tightenable by blocking screws.

Preferably, the second support comprises two parts joined by screws.

Preferably, between the means for immobilizing the toe and the toe there is placed an elastic pad.

Preferably, in the second support there are positioned, slidably and pivotably in spheroidal joints tightenable by blocking screws, two spatulas for lifting the front of the nail.

Preferably, the means for pressing the middle portion of the nail towards the base have a form of a lever mounted in the first support in a spheroidal joint configured to be blocked by a screw.

Preferably, the base is mounted in a plate forming a support for a foot.

Preferably, along the base there are formed protrusions configured to be positioned in grooves of the plate.

Preferably, the means for immobilizing the toe have a form of screws configured to press the toe towards the base.

Preferably, the means for manipulating at the lateral edges of the nail have a form of hooks configured to lift the lateral edges of the nail.

Preferably, the means for manipulating at the lateral edges of the nail have a form of deflecting spatulas configured to deflect aside the flesh of the lateral nail folds.

Preferably, the means for manipulating at the front part of the nail have a form of spatulas configured to lift the front edge of the nail.

Preferably, the means for pressing the middle portion of the nail towards the base have a form of a lever.

Another object of the invention is a method for cosmetic correction of ingrowing foot nails, wherein by using a device for correcting ingrowing nails, the device comprising means for immobilizing the toe with respect to the base, means pressing the middle portion of the nail towards the base, slidable and pivotable means for manipulating at the lateral edge of the nail and slidable and pivotable means for manipulating at the front portion of the nail, the toe is immobilized, the middle portion of the nail is pressed towards the base and the nail and/or the flesh of the nail folds is shaped to a desired shape, the nail is coated with a layer of hardenable material, the hardenable material is left to harden and then the toe is removed from the device.

MODES FOR CARRYING OUT THE INVENTION

First Mode of the Invention

The device for correcting ingrowing nails according to the first embodiment as shown in FIGS. 1-4, comprises a base 101 with a first support 102, in which there are mounted two screws 111, 112 for pressing the toe and two hooks 131, 132 which are slidable and pivotable. The hooks 131, 132 are positioned and immobilized in spheroidal joints 133, 134 which are pressed by hook-blocking screws 135, 136. The toe-pressing screws 111, 112 and the hooks 131, 132 are positioned symmetrically with respect to a lever 121 for pressing the nail which is also mounted in the support 102. The nail-pressing lever 121 is positioned pivotably at the axis of the support 102, and the pressing force is regulated by a screw 123 for regulating the pressing of the nail. Moreover, between the nail-pressing screws 111, 112 and the toe there is placed an elastic pad 114. The base 101 further comprises a second support 103 for spatulas, mounted opposite the first support 102. The second support 103 comprises two parts combined by mounting screws 105, between which a spatula 141 is mounted slidably and pivotably. The spatula 141 is immobilized in a spheroidal joint 143 which is tightened by a spatula-blocking screw 145. The handle 146 of the spatula 145 has a coarse surface.

In place of the hooks 131, 132 for lifting the sides of the nail plate there can be used deflecting spatulas for deflecting asides the flesh of the lateral nail folds.

The hooks 131, 132 allow to lift the lateral edges of the nail, which is particularly useful for correcting involuted nails. The spatula 141 allows to lift the front edge of the nail or to form an extension for an inappropriately cut nail, which is particularly effective when correcting a nail ingrowing to the proximal nail fold.

Second Mode of the Invention

Figure 1:
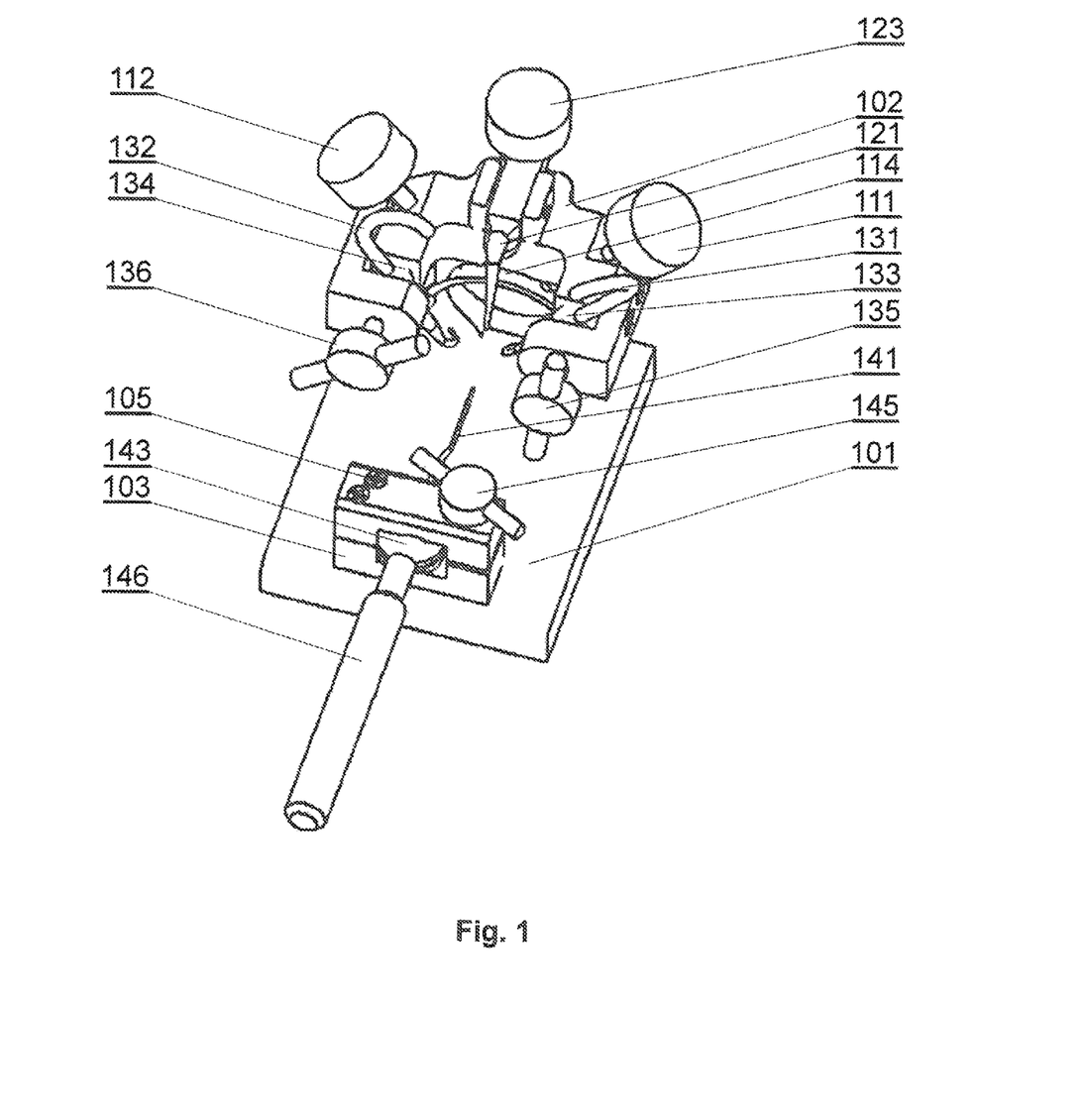
FIGS. 1-4 present a device for correcting nails according to the first embodiment, in a slanted view, front view, side view and top view, respectively.
Figure 2:
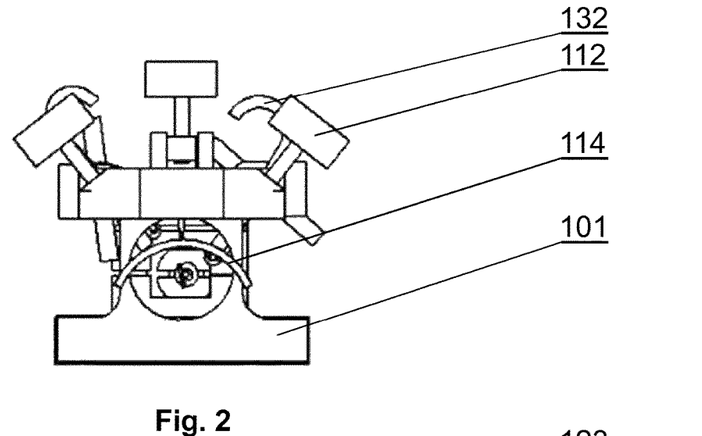
Figure 3:
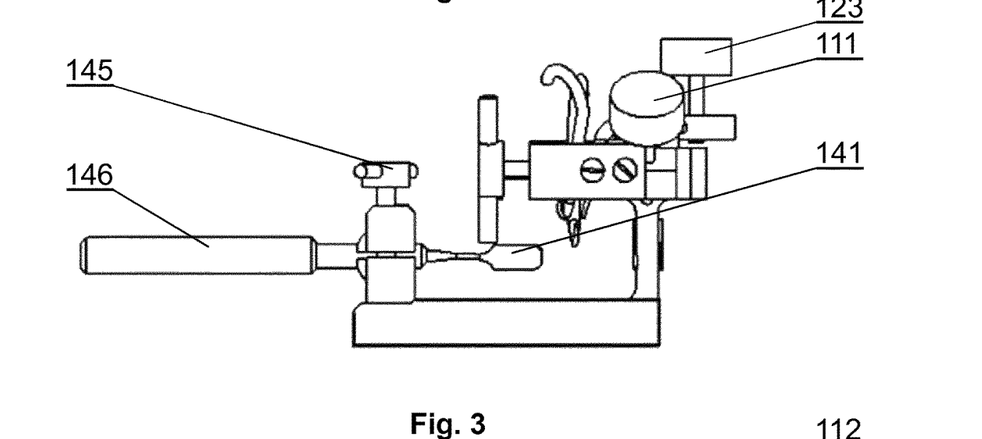
Figure 4:
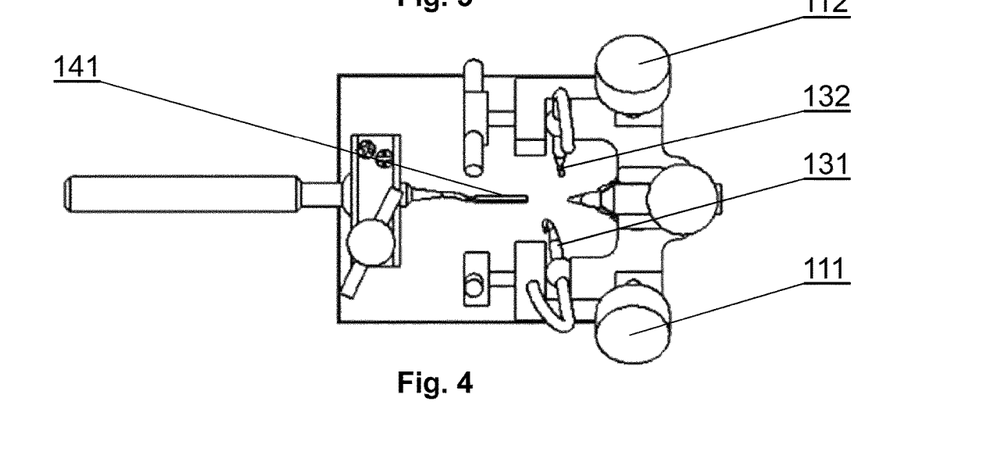
Figure 5:
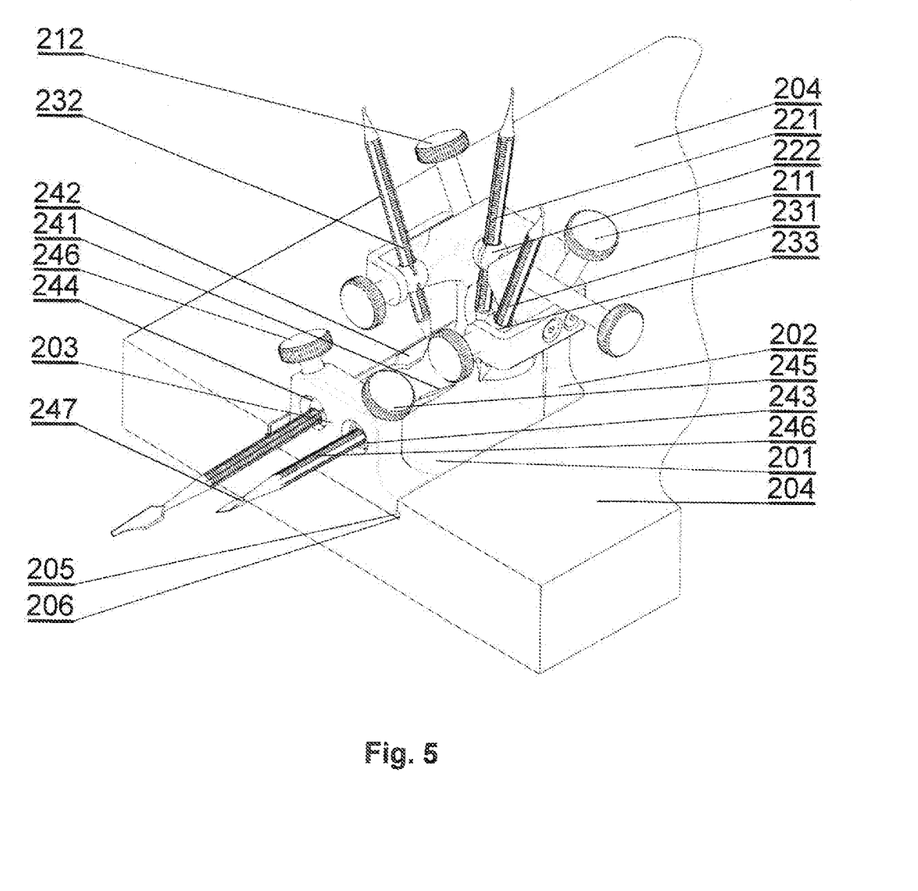
FIG. 5 presents a device for correcting nails according to the second embodiment.

A device for correcting ingrowing nails, according to the second embodiment, as shown in FIG. 5, comprises a base 201 with a first support 202 in which there are mounted two toe-pressing screws 211, 212 and two hooks 231, 232 which are slidable and pivotable. The toe-pressing screws 211, 212 and the hooks 231, 232 are positioned symmetrically with respect to a nail-pressing lever 221, which is also mounted in the support 202. A second support 203 for spatulas is mounted opposite the first support 202. In the second support 203 there are mounted nail-lifting spatulas 241, 242 which are mounted slidably and pivotably in spheroidal joints 243, 244 which are tightened by spatula-blocking screws 245, 246. The pressing lever 221 is mounted in the support 202 in a spheroidal joint 222 which is tightened by a lever-pressing screw 233. Soft pads, for example felt circular pads having a diameter of about 2 cm, can be inserted between the toe-pressing screws 211, 212 and the toe, in order to limit the point wise pressure towards the toe.

Along the base 201 there are protrusions 205 compatible with grooves 206 of a plate 204 for placing a foot, and the base comprises an element for blocking the base 201 in the plate 204. The plate 204 has a size of about 20×30 cm and is made of hard plastic.

In place of the hooks 231, 232 for lifting the sides of the nail plate there can be used deflecting spatulas for deflecting asides the flesh of the lateral nail folds.

The nail-manipulation tools are replaceable and can be selected according to the specifics of the nail being corrected. The replaceability of these tools also allows to sterilize the components for each nail to be corrected.

Exemplary embodiments of the nail-manipulation tools are shown in FIGS. 6-9.

Figure 6:
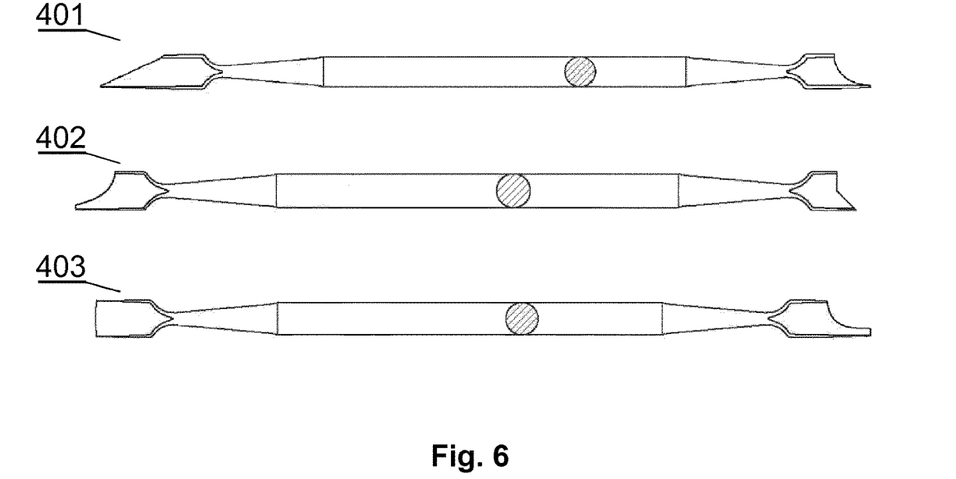
FIG. 6 presents exemplary embodiments of spatulas for lifting the front of the nail plate.

The spatulas for lifting the front edge of the nail may have a form 401-403 as shown in FIG. 6. They may have a handle terminated at both ends by an end. One end may be flat. The other ends may have various arched cutouts, to be selected according to the nail being corrected, the ingrowth depth and the shape of the ingrowth.

Figure 7:
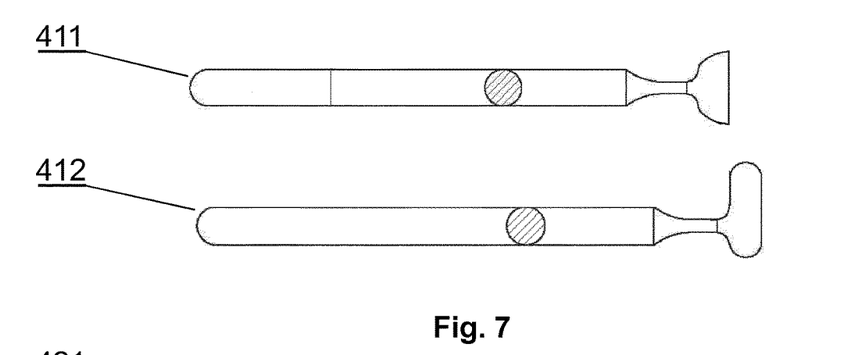
FIG. 7 presents exemplary embodiments of deflecting spatulas.

The deflecting spatulas may have a form 411-412 as shown in FIG. 7. They may have a handle terminated by one flat end and one curved end. These spatulas are used when inflammatory condition occurs at the lateral nail folds. Then, the deflecting spatulas are mounted in the spheroidal joints in place of the hooks. The deflecting spatula is used to deflect the flesh aside and outwards the nail, such as to uncover the lateral edge of the nail. Then, depending on the shape of the missing fragment of the front edge of the nail, a spatula for lifting the front edge of the nail is selected for reconstructing the nail with a hardening material.

Figure 8:
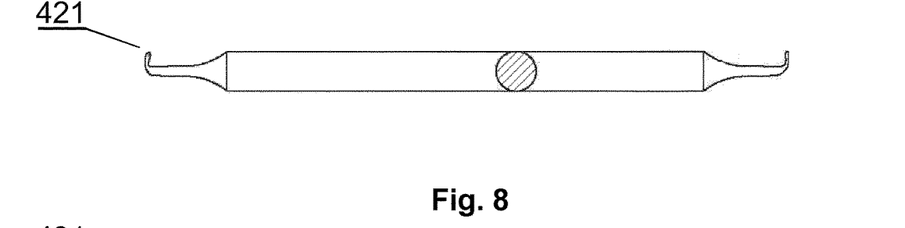
FIG. 8 presents an exemplary embodiment of a hook.

The hooks for lifting the nail edges may have a form 421 as shown in FIG. 8. They may have a handle terminated at both ends with hooks of different inclination.

Figure 9:
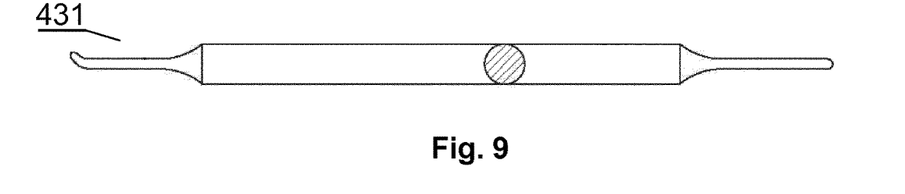
FIG. 9 presents an exemplary embodiment of a lever for pressing the nail.

The lever for pressing the middle portion of the nail towards the base may have a shape 431 as shown in FIG. 9, i.e. it may have a handle with ends of different inclination.

Third Mode of the Invention

Figure 11:
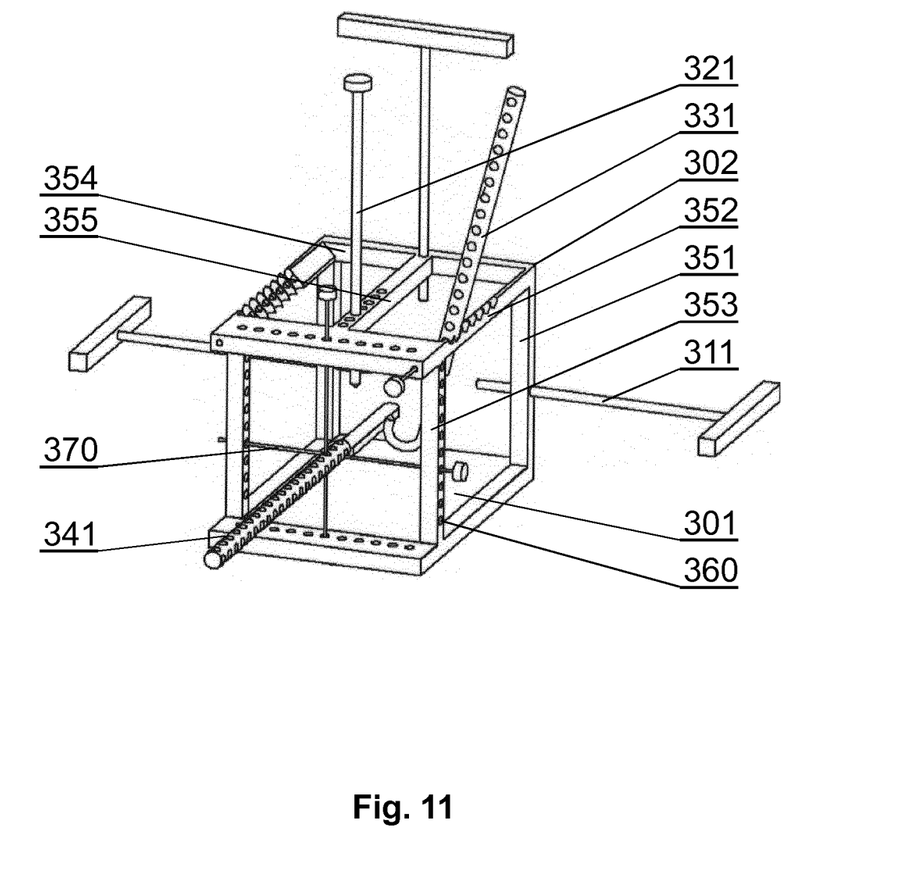
FIG. 11 presents a device for correcting ingrowing nails according to the third embodiment.

The device for correcting ingrowing nails according to the third embodiment is shown in FIG. 11. It comprises a cuboid frame with a flat base 301. The frame forms a support 302 made of four vertical bars 351 attached to the base 301, which are joined at the top by two horizontal bars 354 and two top guides 352. A side guide 353 is attached to two neighboring vertical bars 351. A central top guide 355 is mounted to the two top horizontal bars 354. The guides 353, 352 and 355 have openings 360 made therein. In the support 302, in the openings 360 of the top central guide 355 there are mounted toe-immobilizing means 311 and nail-pressing means 321 towards the base. In the openings 360 of the top central guide 355 there is placed a slidable and pivotable spatula 341 for lifting the front edge of the nail. In the top guides 352 there is mounted slidably and pivotably a hook 331 for lifting the lateral edge of the nail. Moreover, in the side guides 353 there are mounded two further means 311 for immobilizing the toe. The positioning of the toe-immobilizing means 311, the spatula 341 and the hook 331 is blocked by blocking pins 370. Along the handle of the lifting spatula 341 there is a row of openings 360.

Features Common to All Modes For Carrying Out the Invention

Figure 10:
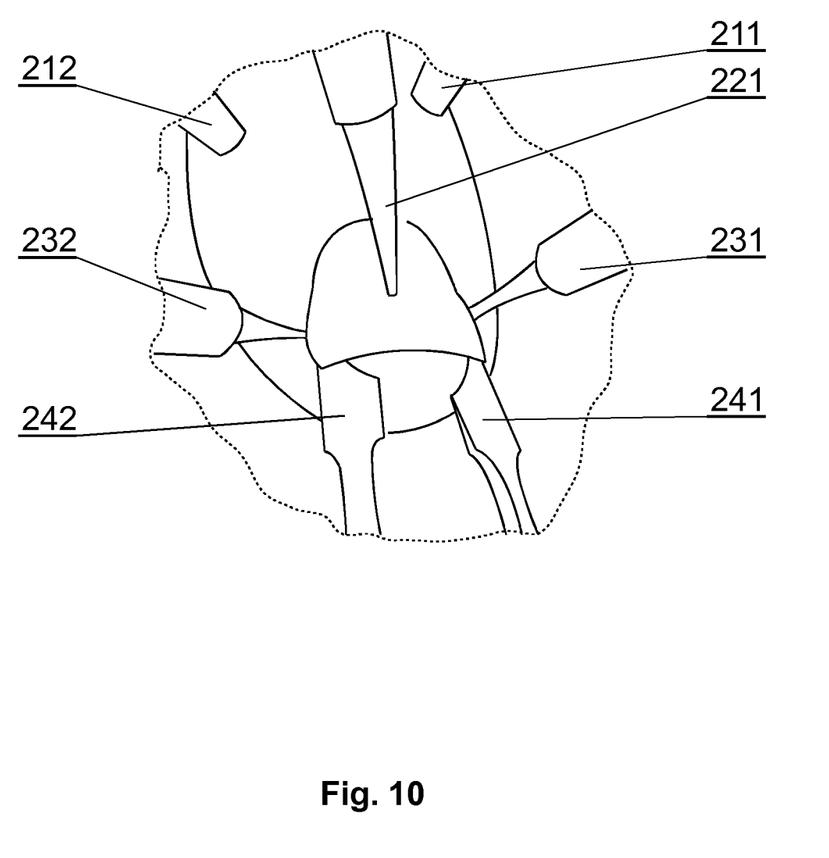
FIG. 10 presents a toe with a nail during correction by the device of the second embodiment.

All the embodiments share the common features such as:
- means 111, 112; 211, 212; 311 for immobilizing the toe with respect to the base 101; 201; 301
- means 121; 221; 321 for pressing the middle portion of the nail towards the base 101; 201; 301, such as a lever 431
- slidable and pivotable means 131, 132; 231, 232; 331 for manipulating at the lateral edge of the nail, which may have a form of hooks 421 or deflecting spatulas 411, 412
- slidable and pivotable means 141; 241, 242; 341 for manipulating at the front edge of the nail, which may have a form of spatulas 401-403 for lifting the front of the nail Method For Correction of Ingrowing Nails The correction of ingrowing nails is carried out as follows. After the toe (or another finger) is positioned in the device, it is immobilized by toe-pressing means 111, 112; 211, 212; 311 and the nail is pressed by the means 121; 221; 321 towards the base. Next, the lateral edge of the nail is manipulated. For example, the lateral edges of an ingrowing nail are lifted by the hooks 131, 132; 231, 232; 331. Alternatively, in case of an inflammatory condition, the flesh along the lateral edges of the nail is deflected aside by deflecting spatulas. Next, by means of one spatula 141; 341 or two spatulas 241, 242 the nail is lifted at its front in order to shape it appropriately. Next, the nail is coated with a hardening material and the material is left to be cured. Preferably, acryl is used as the hardening material, due to its very good adhesion to the nail and high hardness. Acryl is preferably applied as a layer having a thickness of up to 1 mm. Other hardenable materials can be used, such as a hardenable gel. A nail shaped by hooks and spatulas and coated with acryl in the device of the second embodiment of the present invention is shown schematically in FIG. 10. Next, the nail is machined by grinding. The layer of hardenable material keeps the nail in its correct shape and allows its growth without ingrowing. As the nail grows, it can be filed at the front along with the layer of the hardened material. The end portion of the nail, which is free from the hardened layer, is getting appropriately shaped by the front portion which moves forward. After the whole nail grows, when it is properly shortened at the front, the nail usually achieves a correct shape.

In case of an inflammatory condition, the nail shall be first corrected by means of the deflecting spatulas, and after the inflammatory condition is cured, another correction by means of the lifting hooks shall be made to correct an involuted nail.

The invention claimed is:

1. A device for correcting ingrowing foot nails, characterized in that it comprises a base, on which there are mounted means for immobilizing a toe with respect to the base, means for pressing a middle portion of a nail towards the base, slidable and pivotable means for manipulating at a lateral edge of the nail and slidable and pivotable means for manipulating at a front portion of the nail, wherein the means for manipulating at the front portion of the nail are held in spheroidal joints and tightenable by blocking screws.

2. The device according to claim 1, characterized in that it comprises two opposite supports comprising a first support and a second support, mounted on the base, wherein the means for immobilizing the toe with respect to the base comprise two screws mounted on the first support, and wherein the slidable and pivotable means for manipulating at the lateral edge of the nail are positioned symmetrically with respect to the means for pressing the middle portion of the nail, and wherein the second support comprises the pivotable and slidable means for manipulating at the front portion of the nail.

3. The device according to claim 2, characterized in that the means for pressing the middle portion of the nail are mounted pivotably in the first support, and a pressing force is adjustable by a screw for regulating the pressing of the nail.

4. The device according to claim 2, characterized in that the means for manipulating at the lateral edge of the nail are held in spheroidal joints tightenable by blocking screws.

5. The device according to claim 2, characterized in that the second support comprises two parts joined by screws.

6. The device according to claim 2, characterized in that in the second support there are positioned, slidably and pivotably in spheroidal joints tightenable by blocking screws, two spatulas for lifting the front of the nail.

7. The device according to claim 2, characterized in that the means for pressing the middle portion of the nail towards the base have a form of a lever mounted in the first support in a spheroidal joint configured to be blocked by a screw.

8. The device according to claim 1, characterized in that an elastic pad is configured to be placed between the means for immobilizing the toe and the toe.

9. The device according to claim 1, characterized in that the base (201) is mounted in a plate forming a support for a foot.

10. The device according to claim 9, characterized in that along the base there are formed protrusions configured to be positioned in grooves of the plate.

11. The device according to claim 1, characterized in that the means for immobilizing the toe have a form of screws configured to press the toe towards the base.

12. The device according to claim 1, characterized in that the means for manipulating at the lateral edges of the nail have a form of hooks configured to lift the lateral edges of the nail.

13. The device according to claim 1, characterized in that the means for manipulating at the lateral edges of the nail have a form of deflecting spatulas configured to deflect aside flesh of lateral nail folds.

14. The device according to claim 1, characterized in that the means for manipulating at the front portion of the nail have a form of spatulas configured to lift the front portion of the nail.

15. The device according to claim 1, characterized in that the means for pressing the middle portion of the nail towards the base have a form of a lever.

16. A method for cosmetic correction of ingrowing foot nails, characterized in that by using a device for correcting ingrowing nails, the device comprising means for immobilizing a toe with respect to a base, means for pressing a middle portion of a nail towards the base, slidable and pivotable means for manipulating at a lateral edge of the nail and slidable and pivotable means for manipulating at a front portion of the nail, the toe is immobilized, the middle portion of the nail is pressed towards the base and the nail and/or the flesh of the nail folds is shaped to a desired shape, the nail is coated with a layer of hardenable material, the hardenable material is left to harden and then the toe is removed from the device.

* * * * *